United States Patent
Ohnishi et al.

(10) Patent No.: US 7,404,811 B2
(45) Date of Patent: Jul. 29, 2008

(54) DISPOSABLE GARMENT COMPRISING MELTBLOWN NONWOVEN BACKSHEET

(75) Inventors: Kazuyuki Ohnishi, Takaishi (JP); Hiroyuki Ohgata, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/716,150

(22) Filed: Mar. 9, 2007

(65) Prior Publication Data

US 2007/0203469 A1 Aug. 30, 2007

Related U.S. Application Data

(63) Continuation of application No. 10/168,883, filed as application No. PCT/US00/34830 on Dec. 20, 2000, now Pat. No. 7,195,621.

(30) Foreign Application Priority Data

Dec. 22, 1999 (WO) .................... PCT/US99/30624

(51) Int. Cl.
- *A61F 13/00* (2006.01)
- *A61F 13/15* (2006.01)
- *D04H 1/56* (2006.01)

(52) U.S. Cl. ............... 604/385.23; 604/385.01; 604/385.26; 442/400

(58) Field of Classification Search ........... 442/40; 604/385.23, 385.25, 385.26

See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,978,185 A | 8/1976 | Buntin et al. | |
| 4,573,986 A | 3/1986 | Minetola et al. | |
| 4,578,068 A | 3/1986 | Kramer et al. | |
| 4,610,678 A | 9/1986 | Weisman et al. | |
| 4,622,259 A | 11/1986 | McAmish et al. | |
| 4,673,402 A | 6/1987 | Weisman et al. | |
| 4,785,996 A | 11/1988 | Ziecker et al. | |
| 4,834,735 A | 5/1989 | Alemany et al. | |
| 4,842,666 A | 6/1989 | Werenicz | |
| 4,888,231 A | 12/1989 | Angstadt | |
| 5,151,092 A | 9/1992 | Buell et al. | |
| 5,556,751 A | 9/1996 | Stefano | |
| 5,582,903 A | 12/1996 | Levy et al. | |
| 7,195,621 B2 * | 3/2007 | Ohnishi et al. | 604/385.23 |

FOREIGN PATENT DOCUMENTS

CA 2040503 A1 10/1991

* cited by examiner

*Primary Examiner*—Lynda Salvatore
(74) *Attorney, Agent, or Firm*—Richard L. Alexander; Matthew P. Fitzpatrick; Ken K. Patel

(57) ABSTRACT

A disposable garment includes a nonwoven backsheet formed by melt-blowing. The melt-blown nonwoven web has a basis weight of from about 3 g/m² to about 60 g/m² and an air permeability value of at least about 15 cm³/cm²/sec. The melt-blowing web is made by fine fibers having an average fiber diameter of from about 3 μm to about 10 μm

13 Claims, 6 Drawing Sheets

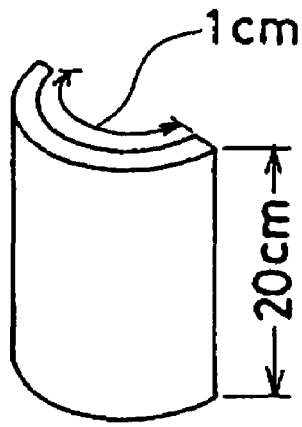 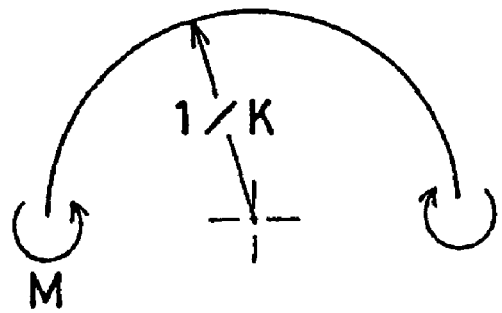
Fig. 3A　　　　　　　　　　Fig. 3B
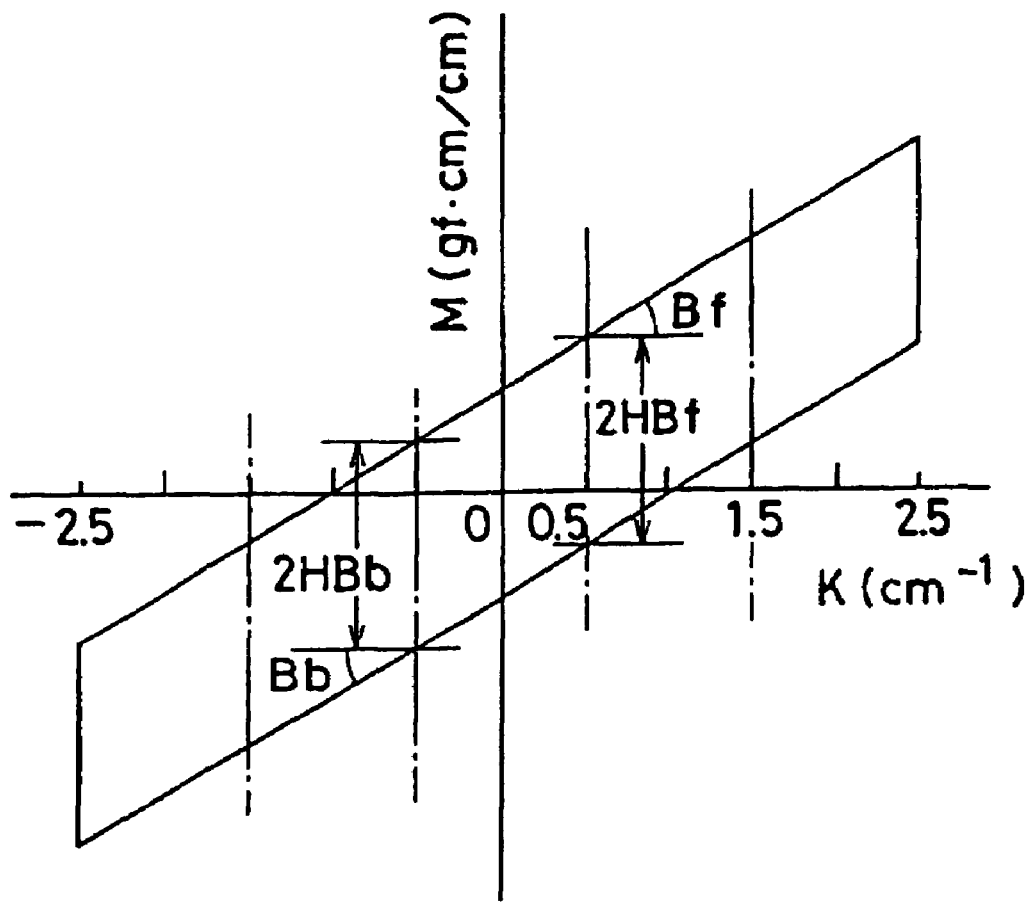
Fig. 4

DISPOSABLE GARMENT COMPRISING MELTBLOWN NONWOVEN BACKSHEET

CROSS REFERENCE TO RELATED APPLICATIONS

This application is a continuation of application Ser. No. 10/168,883, filed Jun. 21, 2002 now U.S. Pat. No. 7,195,621, which is the National Stage of International Application No. PCTUS00/34830, filed Dec. 20, 2000, which claims priority from International Application No. PCTUS99/30624, filed Dec. 22, 1999, the substances of which are incorporated herein by reference.

FIELD OF THE INVENTION

The present invention relates to disposable garments. More specifically, the present invention relates to disposable garments having a meltblown nonwoven backsheet.

BACKGROUND OF THE INVENTION

Infants and other incontinent individuals wear disposable garments such as diapers to receive and contain urine and other body exudates. Disposable garments function either or both to contain the discharged materials and to isolate these materials from the body of the wearer, and from the wearer's garments and bed clothing. Disposable garments having many different basic designs are known to the art. Examples of such disposable garments include disposable diapers (adult and baby) including pull-on diapers and training pants, disposable underwear, and disposable absorbent pads.

It is also known that the exterior of disposable garments may be covered with a flexible, liquid-impervious sheet to prevent any absorbed liquid from passing through the disposable garments and soiling adjacent articles such as clothing, bedding and the like. Such a liquid-impervious sheet is often constructed from polyethylene films and the like. While such sheets prevent liquid from passing through the disposable garment, such a plastic film tends to be uncomfortable for the wearer and/or user. A plastic film may possess insufficient moisture breathability and almost no air permeability, and may therefore cause wearers undesirable skin irritation.

One approach to provide a sufficient amount of moisture breathability is to use a microporous polyfilm. However, such an approach may provide only limited moisture breathability to wearers, sometimes less than 50% of the desired level, and still provide no or almost no air permeability.

Another approach is the use of nonwoven materials. See unexamined Japanese publication (kokai) H03-240151, filed on Feb. 16, 1990, by Asahi Kasei Kogyo, which discloses sanitary materials comprising a melt-blown nonwoven liquid-impermeable sheet made of fine fibers having an average diameter of from 0.5 to 2.5 µm. Although a sheet having such small fibers may retain liquid within the garment, such a sheet does not possess the desired level of air permeability, because the pores are too small. The sheet also tends to lower a tensile strength.

Based on the foregoing, the need exists for a disposable garment having a nonwoven backsheet formed by melt-blowing, which can provide desirable moisture breathability, desirable air permeability, and a tensile strength sufficient for converting to make disposable garments.

SUMMARY OF THE INVENTION

The present invention is directed to a disposable garment comprising a backsheet comprising a melt-blown nonwoven web. The melt-blown web is made from fine fibers having an average fiber diameter of from about 3 µm to about 10 µm. The backsheet has a basis weight of from about 3 g/m$^2$ to about 60 g/m$^2$ and an air permeability value of at least about 15 cm$^3$/cm$^2$/sec.

In another aspect, the present invention is directed to a disposable garment comprising a backsheet comprising a melt-blown nonwoven web. The melt-blown nonwoven web is made from fine fibers having an average fiber diameter of from about 3 µm to about 10 µm. The nonwoven web has a web modulus of between 230 gf/mm and 650 gf/mm. The backsheet has an air permeability value of at least about 15 cm$^3$/cm$^2$/sec.

The present invention is also directed to a disposable garment comprising a liquid pervious topsheet, a liquid impervious backsheet combined with the topsheet, and an absorbent core disposed between the topsheet and the backsheet. The backsheet comprises a melt-blown nonwoven web. The melt-blown nonwoven web has a basis weight of from about 3 g/m$^2$ to about 60 g/m$^2$. The melt-blown nonwoven web is made from polyolefin fine fibers having an average fiber diameter of from about 3 µm to about 10 µm, and have an air permeability value of at least about 15 cm$^3$/cm$^2$/sec.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

FIGS. 3A and 3B are schematic diagrams explaining the measurement for the bending property;

FIG. 4 is a graph showing the bending property of a sample nonwoven;

DETAILED DESCRIPTION OF THE INVENTION

Figure 1:
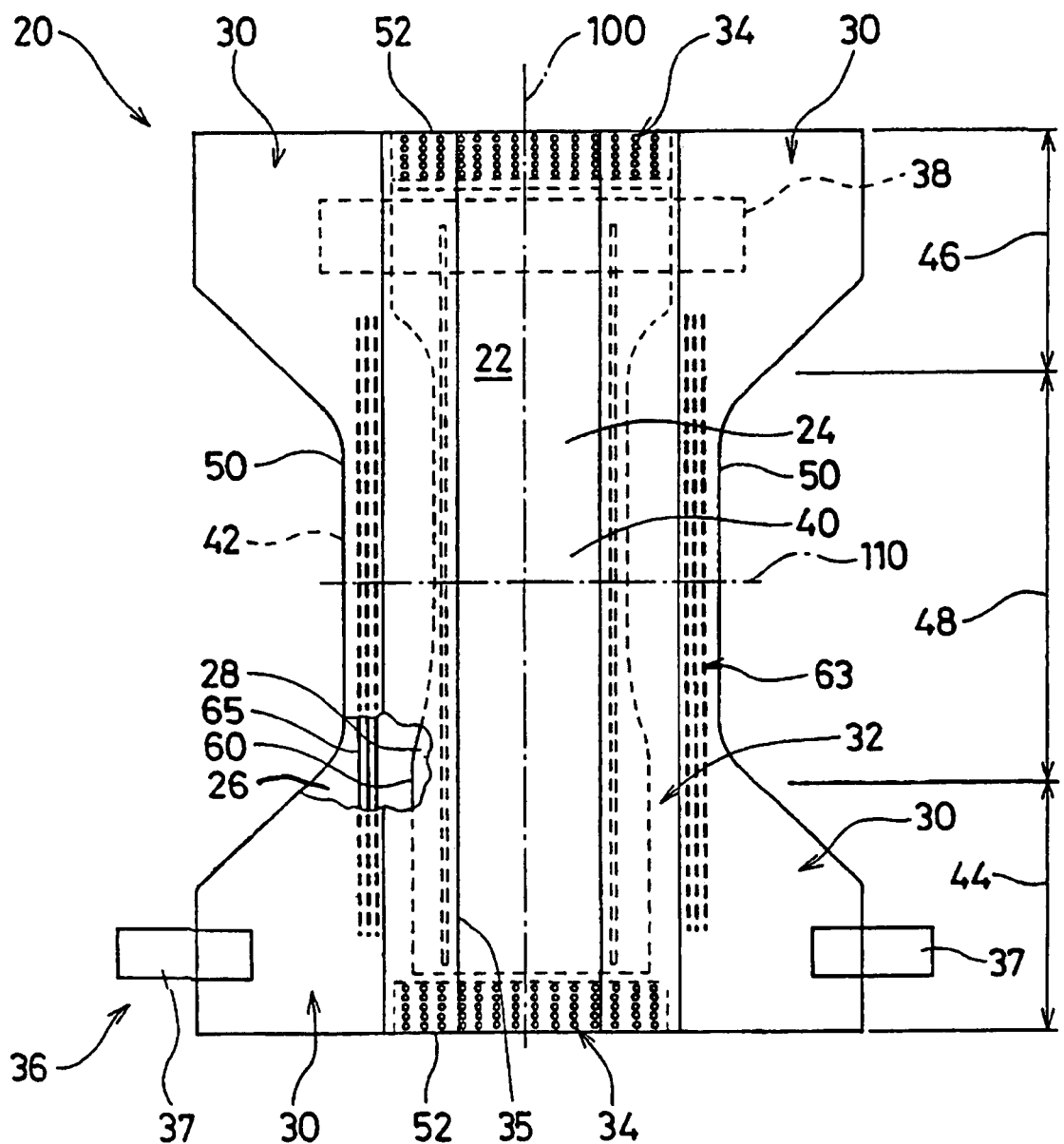
FIG. 1 is a plan view of one preferred embodiment of the disposable garment of the present invention having portions cut away to reveal underlying structure, the inner surface of the garment is facing the viewer.

All cited references are incorporated herein by reference in their entireties. Citation of any reference is not an admission regarding any determination as to its availability as prior art to the claimed invention. The figures herein are not necessarily drawn to scale.

Herein, "comprising" means that other element(s) and step(s) which do not affect the end result can be added. This term encompasses the terms "consisting of" and "consisting essentially of."

Herein, "disposable" describes articles which are not intended to be laundered or otherwise restored or reused as a garment (i.e., they are intended to be discarded after a single use and, preferably, to be recycled, composted or otherwise disposed of in an environmentally-compatible manner).

Herein, "disposable garment," refers to articles which include disposable diapers (adult and baby) including pull-on diapers and training pants, disposable underwear, and disposable absorbent pads.

The present invention can include a variety of disposable garments in need of a backsheet which possesses both liquid-impermeability and moisture breathability/air permeability. The backsheet of the present invention comprises a nonwoven web having a basis weight of from about 3 $g/m^2$ to about 60 $g/m^2$ in combination with an air permeability value of at least about 15 $cm^3/cm^2/sec$. A nonwoven web which has these combined properties provides desirable liquid-impermeability and moisture breathability/air permeability when used in the garments, as well as other significant benefits, such as softness and flexibility.

The nonwoven web herein is made by melt-blowing process, of polyolefin fine fibers having an average fiber diameter of from about 3 µm to about 10 µm. It is known that nonwoven webs made by melt-blowing process provide soft feel, but the strength of these webs is less than webs made by other processes. These melt-brown sheets tend to be broken easily during the manufacturing process of garments. Webs made by small fibers are also believed to be broken easily.

Further, it is believed that webs made by melt-blowing process provide desirable printing, e.g., multicolor registered graphics, to enhance their appearance and consumer acceptance. This is because such web has properties of higher web modulus than polyfilm and other kinds of nonwovens, which permits ease of tension control easily and graphics adjustment to the expected position. Nonlimiting examples of processes for making meltblown nonwoven webs are disclosed in U.S. Pat. No. 3,978,185, Buntin, et al., issued on Aug. 31, 1976; and U.S. Pat. No. 4,622,259, McAmish, et al., issued on Nov. 11, 1986. Such a web is generally a single layer web.

Preferably, the nonwoven web made of a fine fiber herein is selected from the group consisting of a synthetic fine fiber, such as a polyolefin fine fiber, a styrenic thermoplastic elastomer fine fiber, and mixtures thereof, more preferably the synthetic fine fiber is selected from a polypropylene (PP) fine fiber, a polyethylene (PE) fine fiber, and fine fibers formed from random copolymers of ethylene/propylene, and even more preferably the synthetic fine fiber is a polypropylene (PP) fine fiber.

Preferably, the polyolefin fine fiber useful herein has an average fiber diameter of from about 3 µm to about 5 µm. Without intending to be limited by theory, it is believed that a nonwoven web made of such fine fibers provides a desirable liquid impermeability and/or cloth-like feeling, and also retains desirable moisture breathability. In one preferred embodiment, the nonwoven web comprises more than 50 wt % of polypropylene fine fibers.

Preferably, the nonwoven web useful herein has a basis weight of from about 10 $g/m^2$ to about 30 $g/m^2$, and more preferably from about 15 $g/m^2$ to about 25 $g/m^2$.

In addition, the nonwoven web of the present invention has an air permeability value of at least about 15 $cm^3/cm^2/sec$, preferably at least about 20 $cm^3/cm^2/sec$. The air permeability value is determined by using a Frazir type tester described in Section 6.27, entitled "Air Permeability" of Japanese Industrial Standard No. L 1096. The air permeability value is obtained as the air volume which is passed through the specimen (in $cm^3/cm^2/sec$), measured in accordance with the above method.

In one embodiment, the nonwoven web used herein has at least 7,000 $g/m^2/24$ hours, preferably at least 9,000 $g/m^2/24$ hours of moisture breathability. The moisture breathability is determined by the test described in Japanese Industrial Standard No. L 1099.

In another embodiment, the nonwoven web of the present invention preferably has a maximum tensile strength value of at least about 1.0 kgf, more preferably of at least about 1.3 kgf. The maximum tensile strength value is measured and determined according to Section 5.4, entitled "Tensile Strength and Extension Ratio" of Japanese Industrial Standard No. L 1085. The specimen has a length of 30 cm and a width of 5 cm. The specimen holding distance to be measured (i.e., the distance between two holding grips) is 20 cm. The tensile rate is 20 cm/min. The maximum tensile strength value is described as the maximum value of the tensile strength (kgf) measured before the specimen is broken completely.

The nonwoven web of the present invention preferably has a web modulus of between 230 gf/mm and 650 gf/mm, preferably between 300 gf/mm and 550 gf/mm. As used herein, "web modulus" means the mechanical property defined as the slope of the straight line which is connected between 1% strain and 5% strain in a material's stress/strain curve. Web modulus can be measured by the method described herein below. The nonwoven web having a web modulus above do not cause significant variations of strain in the nonwoven web or at least reduce the variation of the strain while the nonwoven web is tensioned for being processed. Therefore, such a nonwoven web allows easy operation of processing the nonwoven web.

In still another embodiment, the nonwoven web of the present invention has an average water resistance value of at least about 250 mm $H_2O$, preferably at least about 400 mm $H_2O$, and more preferably at least about 500 mm $H_2O$. The water resistance value is determined by the "Water Static Pressure Method" described in the section entitled "Testing Methods for Water Resistance of Textiles" of Japanese Industrial Standard No. L 1092. The water resistance value is obtained as an average value of the hydrostatic head value (in mm $H_2O$) measured in accordance with the above method.

The nonwoven web of the present invention is preferably a single layer web when used as a backsheet. Herein, "single layer" refers to a web which comprises one layer and is not joined with another material by chemical or physical means.

In another embodiment of the present invention, the nonwoven backsheet of the present invention may be applied as a two layered structure of the single layer web. Herein, "two layered structure" refers to a structure where at least a part of two single layer webs are joined. Such a two layered structure is preferably formed by folding at least a part of the single layer web. The second layer can also be a fabric made by a conventional processes such as spunbonding or carding processes.

The nonwoven web of the present invention can be further embossed with a pattern formed by a number of discrete bonding spots or areas. Herein, "embossed" refers to a portion of the web which was pressed and/or heated, before it is used to form the disposable absorbent article of the present invention. Herein, "pattern" means that the embossed portion(s) of the web have a predetermined arrangement. The embossed pattern can be any pattern known by those skilled in the art such as spots, lattices, diagonal lines, interrupted lines, and the like. Any embossing process known in the art can be used for forming such an embossed pattern.

As is well known in the art, embossing holds the component fibers together and imparts integrity to the nonwoven web or layer by bonding the component fibers within the nonwoven .web or layer. It is believed that an embossing pattern can increase the strength of the web against friction which is caused between the web and clothes or bedclothes during wearing. The increase in the strength of the web against such friction can be confirmed by Martindale Friction Test.

Preferably, the embossed pattern forms an embossed area (or a bonded area) of at least about 0.5% of the area of the nonwoven sheet. More preferably, the embossed area is from about 1.0% to about 10% of the area of nonwoven sheet.

In a preferred embodiment, the nonwoven web can further include one or more other webs that are joined by physical means, such as melting and that cover the outer side of the web. When joined with other webs, the joined surface preferably contains no-embossing.

Additionally, the nonwoven web of the present invention may have an average bending force value ("BFV") of less than about 80 mg cm$^2$/cm, preferably less than about 50 mg cm$^2$/cm, and more preferably less than about 20 mg cm$^2$/cm. The process for measuring the BFV is measured by the method hereinbelow.

The nonwoven web of the present invention preferably has high level of whiteness which is effective as a background of graphics to help to show vivid and clear colors. The value of whiteness (W) of the nonwoven is preferably not less than 85. The value of the whiteness (W) is measured by the method described herein.

The nonwoven web of the present invention may be printed with graphics using inks. The graphics may be printed by any known methods, such as gravure, offset, and flexo graphics. Flexo graphics are preferred. The examples of inks which can be used for printing are FPOT and P-BEST (produced by Osaka Printing Ink MFG. Co., Ltd.) and XS-787 (produced by Dainippon Ink and Chemicals, Incorporated). In order to maintain the air permeability and/or the moisture breathability of the nonwoven web, it is preferable that the basis weight of the ink is less than 20 g/m$^2$, more preferably between 0.3 g/m$^2$ and 5 g/m$^2$.

In a preferred embodiment, the disposable garment of the present invention is an unitary disposable diaper 20, shown in FIG. 1. Herein, "unitary" refers to garments which are formed of separate parts united together to form a coordinated entity so that they do not require separate manipulative parts like a separate holder and liner. Herein, "diaper" refers to an garment generally worn by infants and incontinent persons that is worn about the lower torso of the wearer. It should be understood, however, that the present invention is also applicable to other disposable garments such as incontinence briefs, incontinence undergarments, diaper holders and liners, training pants, and the like.

FIG. 1 is a plan view of the diaper 20 in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges 60, an inner surface and an outer surface. The diaper preferably further comprises side panels 30; elasticized leg cuffs 32; elasticized waistbands 34; and a fastening system 36 preferably comprising a pair of securement members 37 and a landing member 38. The backsheet 26 prevents the exudates absorbed and contained in the absorbent core 28 from wetting articles which contact the diaper 20 such as bed sheets and undergarments.

The diaper 20 has an inner surface 40 (facing the viewer in FIG. 1), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24).

The outer surface 42 comprises that portion of the diaper 20 which is positioned away from the wearer's body (i.e., the outer surface 42 is generally formed by at least a portion of the backsheet 26 and other components joined to the backsheet 26). Herein, "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 100 and a transverse centerline 110. Herein, "longitudinal", refers to a line, axis, or direction in the plane of the diaper 20 that is generally aligned with (e.g., approximately parallel with) a vertical plane which bisects a standing wearer into left and right halves when the diaper 20 is worn. Herein, "transverse", refers to an interchangeable line, axis or direction which lies within the plane of the diaper that is generally perpendicular to the longitudinal direction; which divides the wearer into front and back body halves.

The topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003, entitled "Contractible Side Portions for Disposable Diaper," Buell, issued on Jan.14, 1975; and U.S. Pat. No. 5,151,092, entitled "Absorbent Article With Dynamic Elastic Waist Feature Having A Predisposed Resilient Flexural Hinge," Buell et al., issued on Sep. 29, 1992.

The backsheet 26 of the present invention is positioned adjacent the outer surface of the absorbent core 28 and is preferably joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258.

An example of a suitable attachment means includes an open pattern network of filaments of adhesive. See, U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and process shown in U.S. Pat. No. 3,911,173, Sprague, Jr., issued on Oct. 7, 1975; U.S. Pat. No. 4,785,996, Ziecker, et al., issued on Nov. 22, 1978; and U.S. Pat. No. 4,842,666, Werenicz, issued on Jun. 27, 1989.

Alternatively, the attachment means may comprise heat bonds, pressure bonds, ultrasonic bonds, dynamic mechanical bonds, or any other suitable attachment means or combinations of these attachment means as are known in the art.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has an outer-facing (or garment-facing) side, a body-facing side, a pair of side edges, and a pair of waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other garments such as comminuted wood pulp which is generally referred to as airfelt. Examples of other suitable garments include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

A preferred embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678, entitled "High-Density Absorbent Structures," Weisman et al., issued on Sep. 9, 1986; U.S. Pat. No. 4,673,402, entitled "Absorbent Articles With Dual-Layered Cores," Weisman et al., issued on Jun. 16, 1987; U.S. Pat. No. 4,888,231, entitled "Absorbent Core Having A Dusting Layer," Angstadt, issued on Dec. 19, 1989; and U.S. Pat. No. 4,834,735, entitled "High Density Absorbent Members Having Lower Density and Lower Basis Weight Acquisition Zones," Alemany et al., issued on May 30, 1989.

The absorbent core may further comprise the dual core system containing an acquisition/distribution core of chemically stiffened fibers positioned over an absorbent storage core, thereby forming a dual core system. In a preferred embodiment, the chemically stiffened fibers are hydrophilic chemically stiffened cellulosic fibers. Herein, "chemically stiffened fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains. For example, crosslinking agents can be applied to the fibers which, then form intrafiber crosslinked bonds. These crosslinked bonds increase the stiffness of the fibers. Whereas the utilization of intrafiber crosslinked bonds to chemically stiffen the fibers is preferred, it is not meant to exclude other types of reactions for chemical stiffening of the fibers.

In more preferred stiffened fibers, chemical processing includes intrafiber crosslinking with crosslinking agents while such fibers are in a relatively dehydrated, defibrated (i.e., individualized), twisted, and curled condition. Suitable chemical stiffening agents include monomeric crosslinking agents including, but not limited to, $C_{2-8}$ dialdehydes and $C_{2-8}$ monoaldehydes having an acid functionality, which can be employed to form a crosslinking solution. These compounds are capable of reacting with at least two hydroxyl groups in a single cellulose chain or on proximately-located cellulose chains within a single fiber.

Preferred crosslinking agents useful herein for preparing stiffened cellulose fibers include, but are not limited to, glutaraldehyde, glyoxal, formaldehyde, glyoxylic acid, and polycarboxylates, such as citric acid. The polycarboxylic stiffening agents and a process for making stiffened fibers from them are described in U.S. Pat. No. 5,190,563, entitled "Process for Preparing Individualized, Polycarboxylic Acid crosslinked Fibers," Herron, issued on Mar. 2, 1993. The effect of crosslinking under these conditions is to form fibers which are stiffened and which tend to retain their twisted, curled configuration during use in the disposable garment herein.

Preferred dual core systems are disclosed in U.S. Pat. No. 5,234,423, entitled "Absorbent Article With Elastic Waist Feature and Enhanced Absorbency," Alemany, et al., issued on Aug. 10, 1993; and U.S. Pat. No. 5,147,345, entitled "High Efficiency Absorbent Articles For Incontinence Management," Young, et al., issued on Sep. 15, 1992. In a preferred embodiment, the acquisition and/or distribution core includes chemically treated stiffened cellulosic fiber material, available from Weyerhaeuser Co. (U.S.A.) under the trade designation of "CMC." Preferably, the acquisition/distribution core has a basis weight of from about 40 $g/m^2$ to about 400 $g/m^2$, and more preferably from about 75 $g/m^2$ to about 300 $g/m^2$.

The topsheet 24 is preferably positioned adjacent the inner surface of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The topsheet 24 is preferably made of a hydrophobic material to isolate the wearer's skin from liquids which have passed through the topsheet 24 and are contained in the absorbent core 28 (i.e., to prevent rewetting). If the topsheet is made of a hydrophobic material, at least the upper surface of the topsheet is treated to be hydrophilic so that liquids will transfer through the topsheet more rapidly. This increases the likelihood that body exudates will be drawn through the topsheet and absorbed by the absorbent core, before they flow off of the topsheet.

The topsheet 24 can be rendered hydrophilic by treating it with a surfactant. Suitable process for treating the topsheet with a surfactant include spraying the topsheet material with the surfactant and immersing the material into the surfactant. A more detailed discussion of such a treatment and hydrophilicity is contained in U.S. Pat. No. 4,988,344, entitled "Absorbent Articles with Multiple Layer Absorbent Layers," Reising, et al., issued on Jan. 29, 1991 and U.S. Pat. No. 4,988,345, entitled "Absorbent Articles with Rapid Acquiring Absorbent Cores," Reising, issued on Jan. 29, 1991. Alternatively, the topsheet 24 may be a carded nonwoven material which is formed by fibers treated with hydrophilic finishing oil.

An alternative preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, entitled "Absorptive Structures Having Tapered Capillaries," Thompson, issued on Dec. 30, 1975; U.S. Pat. No. 4,324,246, entitled "Disposable Absorbent Article Having A Stain Resistant Topsheet," Mullane, et al., issued on Apr. 13, 1982; U.S. Pat. No. 4,342,314, entitled "Resilient Plastic Web Exhibiting Fiber-Like Properties," Radel et al., issued on Aug. 3, 1982; U.S. Pat. No. 4,463,045, entitled "Macroscopically Expanded Three-Dimensional Plastic Web Exhibiting Non-Glossy Visible Surface and Cloth-Like Tactile Impression," Ahr et al., issued on Jul. 31, 1984; and U.S. Pat. No. 5,006,394, entitled "Multilayer Polymeric Film," Baird, issued on Apr. 9, 1991.

The diaper, 20, preferably further includes elasticized leg cuffs 32 for providing improved containment of liquids and other body exudates. The elasticized leg cuffs may include several different embodiments for reducing the leakage of body exudates in the leg regions. The leg cuffs can be and are sometimes also referred to as leg bands, side flaps, barrier cuffs, elastic cuffs or gasketing cuffs.

U.S. Pat. No. 3,860,003, entitled "Contractable Side Portions for Disposable Diaper," Buell, issued on Jan. 14, 1975, describes a disposable diaper which provides a contractible leg opening having a side flap and one or more elastic members to provide an elasticized leg cuff. U.S. Pat. No. 4,909,803, entitled "Disposable Absorbent Article Having Elasticized Flaps," Aziz, et al., issued on Mar. 20, 1990, describes a disposable diaper having "stand-up" elasticized flaps (barrier cuffs) to improve the containment of the leg regions. U.S. Pat. No. 4,695,278, entitled "Absorbent Article Having Dual Cuffs," Lawson, issued on Sep. 22, 1987 and U.S. Pat. No. 4,795,454, entitled "Absorbent Article Having Leakage-Resistant Dual Cuffs," Dragoo, issued on Jan. 3, 1989, describe disposable diapers having dual cuffs including a gasketing cuff and a barrier cuff. U.S. Pat. No. 4,704,115, entitled "Disposable Waist Containment Garment," Buell, issued on Nov. 3, 1987, discloses a disposable diaper or incontinence garment having side-edge-leakage-guard gutters configured to contain free liquids within the garment. In preferred embodiments, such barrier cuffs or "stand-up" elasticized flaps are formed by the nonwoven layer of the present invention.

Figure 2:
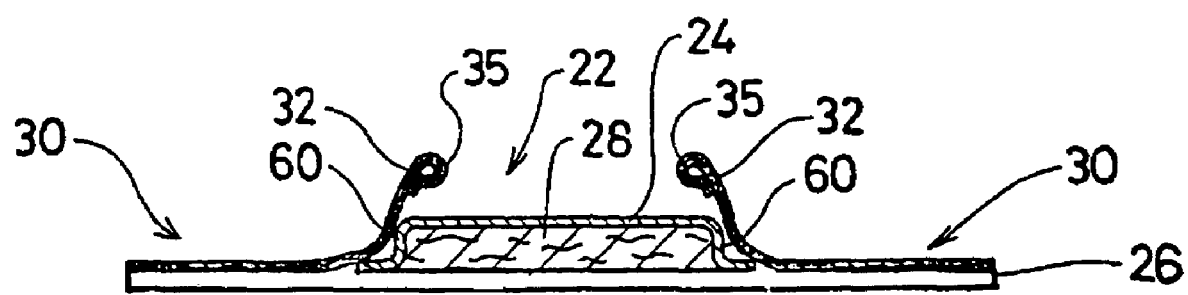
FIG. 2 is an enlarged, cross-sectional view of one embodiment of a disposable garment comprising a backsheet.

FIG. 2 is an enlarged, cross-sectional view of diaper 20 to more clearly show the construction of the diaper 20 comprising the topsheet 24; a liquid impervious backsheet 26 joined to the topsheet; and an absorbent core 28 positioned between the topsheet 24 and the backsheet 26.

While each elasticized leg cuff may be configured so as to be similar to any of the leg bands, side flaps, barrier cuffs, or elastic cuffs described above, it is preferred that the elasticized leg cuff 32, includes an elastic gasketing cuff 63, with one or more elastic strands 65. These are described in the above-referred U.S. Pat. Nos. 4,695,278 and 4,795,454. It is also preferred that each elasticized leg cuff further include an inner barrier cuff 35 which are also described in the above-referenced U.S. Pat. No. 4,909,803.

The diaper 20 further includes an elasticized waistband 34 that provides improved fit and containment. The elasticized waistband is that portion or zone of the pull-on diaper which is intended to elastically expand and contract to dynamically fit the wearer's waist. The elasticized waistband preferably extends longitudinally outwardly from the waist edge of the diaper toward the waist edge of the absorbent core. Preferably, the diaper has two elasticized waistbands, one positioned in the back region and one positioned in the front region. The elasticized waistband may be constructed in a number of different configurations including those described in U.S. Pat. No. 4,515,595, entitled "Disposable Diapers with Elastically Contractible Waistbands," Kievit et al., issued on May 7, 1985 and the above referenced U.S. Pat. No. 5,151,092.

TEST METHODS

Measurements of Water Resistance Value, Air Permeability, Moisture Breathability, and Tensile Strength are carried out by using the following Japanese Standard method (JIS).

| | | |
|---|---|---|
| Moisture Breathability | g/m$^2$/24 hours | L-1099 Method A-1 |
| Water Resistance Value | mmH$_2$O | L-1092 Method A |
| Air Permeability | cm$^3$/cm$^2$/sec | L-1096-6-27-1 Method A |
| Tensile Strength | kgf | L-1096-6-12-1 Method A |

Web Modulus

Web modulus of a test web is measured as follows.

1. Measurement of Tensile Stress of Web (Sample Preparation)

Figure 6:
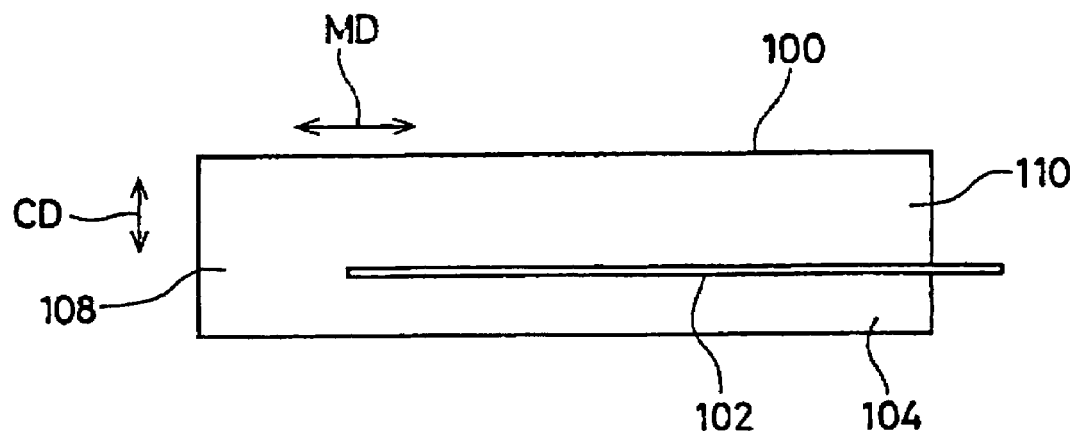
FIG. 6 is a schematic diagram of the first state for tensile stress measurement.

1. Cut a test web into a test piece 100 of 610 mm length in the machine direction (MD) and 150 mm width, place the test piece on a flat table and smooth out flat. (FIG. 6)
2. Place the 9.5 mm diameter steel rod 102 on the test piece 100 in the MD such that its location in the cross direction (CD) should be in about ⅓ the way (about 50 mm) from one longitudinal side 104 of the test piece 100. The rod 102 should stick out of the test piece with about 2.5 cm so that it would be easier to remove it later. (FIG. 6)

Figure 7:
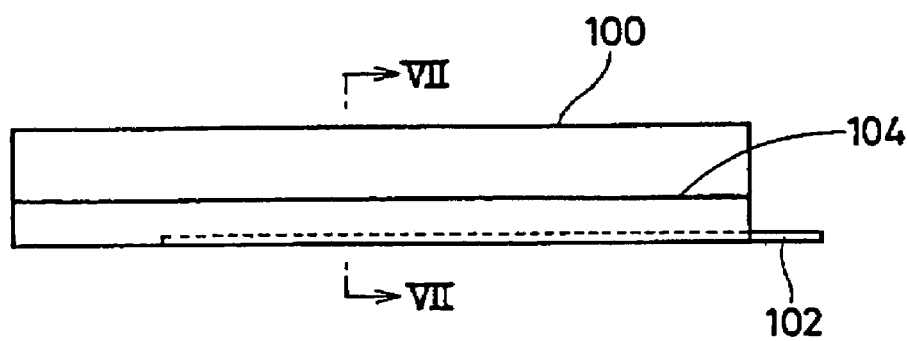
FIG. 7 is a schematic diagram of the second state for tensile stress measurement.
Figure 8:
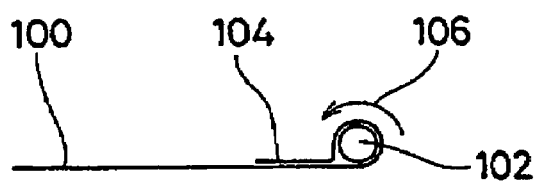
FIG. 8 is a cross sectional view taken along the line VII-VII shown in FIG. 7.
Figure 9:
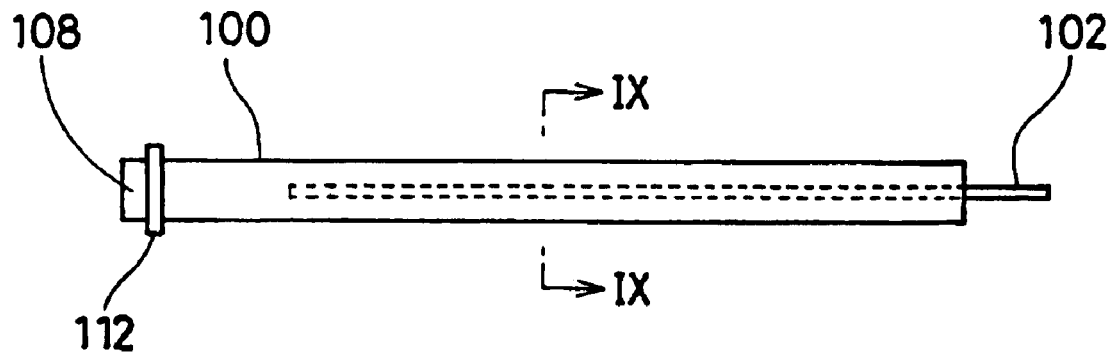
FIG. 9 is a schematic diagram of the third state for tensile stress measurement.
Figure 10:
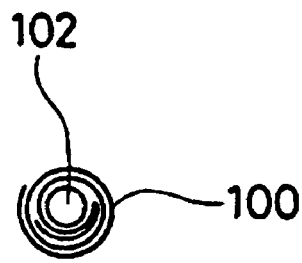
FIG. 10 is a cross sectional view taken along the line IX-IX shown in FIG. 9.
Figure 11:
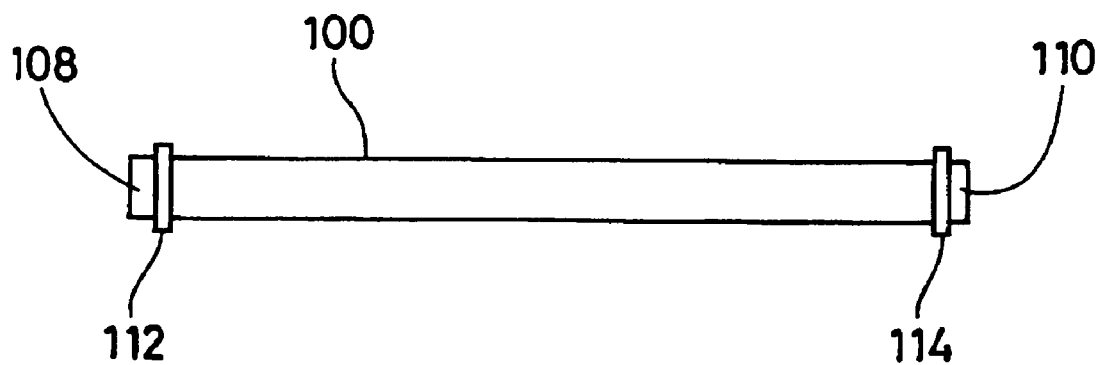
FIG. 11 is a schematic diagram of the fourth state for tensile stress measurement.

3. Fold the side of one longitudinal side 104 of the test piece 100 over the rod 102 along the rod 102 and lay flat (FIG. 7). And then, tuck the test piece 100 around the rod 102 in the CD as shown by the arrow 106 (FIG. 8) and roll up the test piece 100. (FIGS. 9 and 10)
4. Be as careful as possible to avoid wrinkles in the test piece 100 and keep the rod parallel to the longitudinal side of the test piece 100. Flatten the first end edge 108 of the rolled test piece 100 in which the rod 102 is not present. Staple the flattened first end edge 108 several times (staple at the first end edge 108 is designated by the reference number of 112 in FIG. 9) through the multiple layers of the test piece 100 to join these layers so that they will not slip in during the test.
5. Pull the rod out of the second end edge 110 carefully not to let the test piece unwind. Flatten the second end edge 110 such that it is flat in the same plane as the first end edge 108, and staple it several times (staple at the second end edge 110 is designated by the reference number of 114 in FIG. 11) such that the distance between the staples at the first end edge 108 and the second end edge 110 is about 560 mm which is sufficient for the gage length (508 mm) of the tensile tester below. Thus, a test sample is prepared.

(Instrument Set Up)

The instrument (Tensile tester: Instron 5564/MTS, Testworks ver.3.06) is set up to pull the test samples under the following condition.

| | |
|---|---|
| Master method | Tensile |
| Load cell | 100 N |
| Gauge length | 508 mm |
| Cross head speed | 254 mm/minute |
| Points for reading stress | at 1%, and 5% strain |

(Measurement)

The measurement is made according to the following procedure.
1. Insert one end edge of a test sample into the upperjaw of tensile tester and close it.
2. Align the strip between the upper and lowerjaws.
3. Place the other end edge of the test sample into the lower jaw with enough tension to eliminate any slacks.
4. Reset the tension of the cross head (Load meter) of the tensile tester.
5. Close the lower jaw with confirming that the load meter does not indicate more than 5.0 g.
6. Start particular tester.

From the measurement above, tensile stresses of the test sample at 1% and 5% strain are measured.

2. Calculation of Web Modulus

Tensile stresses at 1% and 5% strain are measured with the test method above. The differential of these tensile stresses per unit width is calculated, and then, the differential is divided by 0.04 which means the differential of 5% and 1%. This value is reported as web modulus for each specimen.

Web modulus $(gf/mm)$=(Tensile stress $(gf)$ at 5% strain−Tensile stress $(gf)$ at 1% strain)/((0.05−0.01)·150 $(mm)$)

wherein 150 (mm) is the width of the test piece.

Value of Whiteness (W)

The whiteness is measured with a spectrophotometer, "NF777", made by Nippon Denshoku Ind. Co., Ltd., Japan. W (ASTM E313) is used as the value of whiteness. Whiteness of a material is calculated from CIE (Commission Internatio-nale de l'Eclairage—the International Commission on Illumination) Tristimulus XYZ values in the measurement. The higher this value is, the whiter the sample shows. One layer of each sample is put on the white plate which is prepared by Nippon Denshoku, and then measured by the spectrophotometer.

$$W=4B-3G$$

(G: same as Y value, B=0.847Z of each measured sample)

Leakage Test

1. Under 1 psi

Figure 5:
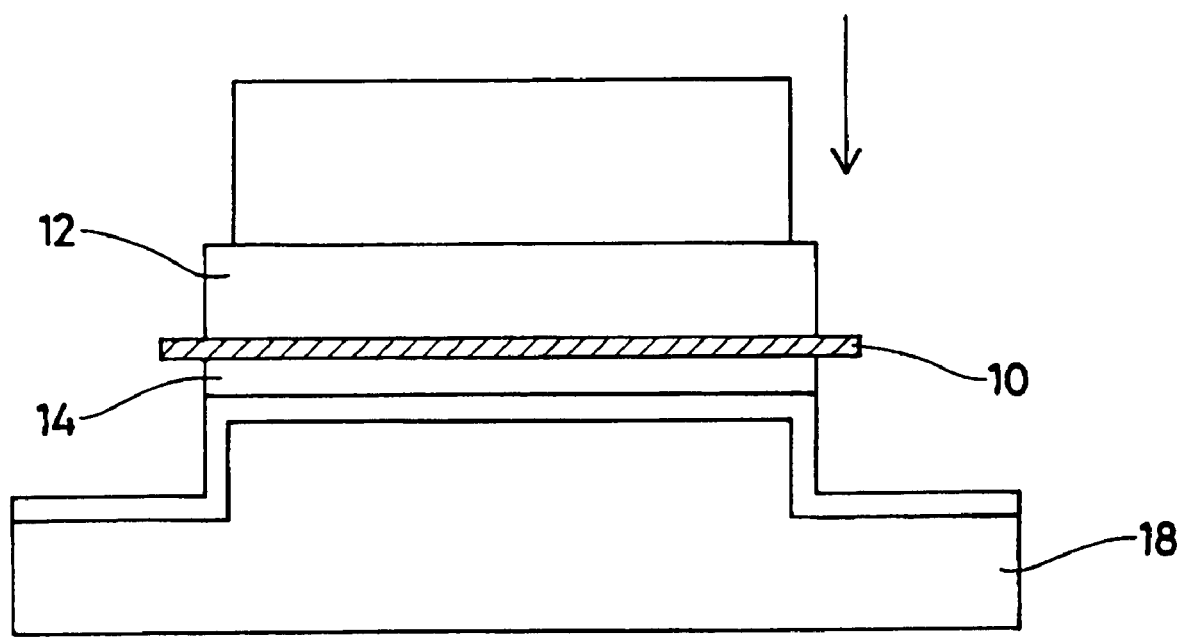
FIG. 5 is a schematic diagram explaining the equipment of the leakage test.

To measure the leakage, the equipment shown in FIG. 5 is used. A weight stand 18 (made by Daishin-seisakusyo, Osaka, Japan) is prepared by wrapping with a polyolefin film.

A core material 12 (airfelt+AGM wrapped with tissue material) and a filter paper 14 (Ahlstrom Filtration 939), having the size of 60 mm×30 mm, are prepared. The filter paper which is just on the weight stand, a test web sample 10, and the core material on the top are placed on the weight stand in order. The airfelt has a weight of about 0.6 g with the size of 60 mm×30 mm and is obtainable from Buckeye Cellulose Corporation in the U.S.A. under the name of Forley Fluff. The AGM has a weight of about 0.4 g and is obtainable from Nippon Shokubai Co., Ltd. in Japan under the name of L-761f. The tissue has a basis weight of 15 g/m² and is obtainable from Havix Co. in Japan under the name of Mini Core Cover Tissue. After setting three materials on the weight stand, 5 ml synthetic urine including water-soluble blue dye is applied onto the core material, then 1 psi pressure is put on them for 180 minutes (3 hours). After 3 hours under 1 psi, color of the filter paper is checked whether the "blue" urine is impregnated to the filter paper through the test web. If the paper color is changed to blue, then, the weight of filter paper, absorbing synthetic urine, coming out from the core material through the test web is measured.

2. Under 10 psi

Except for a 10 psi pressure applied during 30 minutes, the procedure described above is used.

Bending Force Value (BFV)

A bending tester, KES-FB2, Kato Tech. Co Ltd., is used to measure BFV. The deformation mode is a pure bending between the curvature K=−2.5 cm⁻¹ and 2.5 cm⁻¹. The effective dimension for the measurement is 20 cm in length and 1.0 cm in width (rectangular). The specimen is bent as shown in FIGS. 3A and 3B. The bending rate is 0.5 cm⁻¹/sec. As a result, the bending hysteresis curve as shown in FIG. 4 is obtained by the measurement. The horizontal axis shows the curvatures K cm⁻¹ and the vertical axis shows the moment M (gf·cm/cm).

The BFV is calculated as follows:

$$BFV=(Bf+Bb)/2 \qquad (1)$$

where Bf and Bb are the slopes of the hysteresis curves between K=0.5 cm⁻¹ and 1.5 cm⁻¹ and K=−0.5 cm⁻¹ and −1.5 cm⁻¹ respectively.

Measurements are carried out in the MD and CD directions of the same web specimen. The average BFV is the mean value of the above BFV obtained from the measurements about the MD and CD directions of the specimen.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The melt-blown nonwoven webs of the present invention are prepared as follows. The properties are described in Table I.

Example I

A melt-blown nonwoven web having a basis weight of 15 g/m², without an embossing pattern, PC0015G is prepared. The nonwoven web is made of fine fibers of a polypropylene (PP). The fine fibers have the thickness of from about 3 μm to about 5 μm.

This nonwoven web has a water resistance value of 650 mm $H_2O$, a air permeability value of 38.9 cm³/cm²/sec, and a maximum tensile strength value of 1.65 kgf. The embossing ratio (of the embossing roll) is 3.3%. The web modulus of the nonwoven web is 371 gf/mm. The value of whiteness (W) is 88.

Example II

A melt-blown nonwoven web having a basis weight of 15 g/m², with an embossing pattern, PC0015EM is prepared. The nonwoven web is made of fine fibers of a polypropylene (PP). The fine fibers have the thickness of from about 3 μm to about 5 μm.

This nonwoven web has a water resistance value of 680 mm $H_2O$, a air permeability value of 24.5 cm³/cm²/sec, and a maximum tensile strength value of 2.06 kgf. The embossing ratio (of the embossing roll) is 3.3%. The web modulus of the nonwoven web is 493 gf/mm. The value of whiteness (W) is 88.

Example III

A melt-blown nonwoven web having a basis weight of 50 g/m², with an embossing pattern, PC0050A is prepared. The nonwoven web is made of fine fibers of a polypropylene (PP). The fine fibers have the thickness of from about 3 μm to about 5 μm.

This nonwoven web has a water resistance value of 520 mm $H_2O$, a air permeability value of 23.1 cm³/cm²/sec, and a maximum tensile strength value of 2.73 kgf. The embossing ratio (of the embossing roll) is 3.3%. The web modulus of the nonwoven web is 596 gf/mm. The value of whiteness (W) is 90.

TABLE I

|  | Example I | Example II | Example III |
|---|---|---|---|
| Basis Weight (g/m²) | 15 | 15 | 50 |
| Water Resistance Value (mmH₂O) | 650 | 680 | 520 |
| Moisture Breathability (g/m²/24 hours) | 11400 | 11100 | 9970 |
| Air Permeability (cm³/cm²/sec) | 38.9 | 24.5 | 23.1 |
| Maximum Tensile Strength (kgf) | 1.65 | 2.06 | 2.73 |
| Web Modulus (gf/mm) | 371 | 493 | 596 |
| Value of Whiteness (W) | 88 | 88 | 90 |
| Leakage |  |  |  |
| 1. Under 1 psi | no leakage | no leakage | no leakage |
| 2. Under 10 psi | no leakage | no leakage | no leakage |

As shown Table I, the melt-blown nonwoven webs of the present invention provide desirable properties. For example, the nonwoven web of the present invention show high moisture breathability and air permeability, and hydrostatic head values while avoiding leakage of liquid.

It is understood that the examples and embodiments desired herein are for illustration purposes only and for various modifications or changes in light there of will be suggested to one of ordinary skill in the art without departing from the scope of the present invention.

What is claimed is:

1. A disposable garment comprising a liquid pervious topsheet, a liquid impervious backsheet combined with the topsheet, an absorbent core disposed between the topsheet and the backsheet, and an elasticized leg cuff;

wherein the elasticized leg cuff comprises a nonwoven web, wherein the nonwoven web comprises a first layer and a second layer, wherein the first layer comprises fine fibers having an average fiber diameter of from about 3 μm to about 10 μm, wherein the nonwoven web has a basis weight of from about 3 g/m² to about 60 g/m², an air permeability value of at least about 15 cm³/cm²/sec, and a moisture breathability value of at least 7,000 g/m²/24 hours.

2. The disposable garment of claim 1, wherein the first layer comprises polyolefin fine fibers having an average fiber diameter of from about 3 μm to about 5 μm.

3. The disposable garment of claim 1, wherein the nonwoven web has a maximum tensile strength value of at least about 0.7 kgf.

4. The disposable garment of claim 2, wherein the polyolefin is selected from the group consisting of polyethylene, polypropylene, random copolymers of ethylene/propylene, and mixtures thereof.

5. The disposable garment of claim 1, wherein the first layer comprises more than 50 wt % of polypropylene fine fibers.

6. The disposable garment of claim 1, wherein the nonwoven web has a water resistance value of at least about 250 mm $H_2O$.

7. The disposable garment of claim 1, wherein the nonwoven web has a value of whiteness of not less than 85.

8. The disposable garment of claim 1, wherein the disposable garment exhibits no leakage under 10 psi of pressure.

9. The disposable garment of claim 1, wherein the nonwoven web exhibits a web modulus of between 230 gf/mm and 650 gf/mm.

10. The disposable garment of claim 1, wherein the nonwoven web exhibits an average bending force values of less than about 80 mg·cm²/cm.

11. The disposable garment of claim 1, wherein the second layer is a fabric formed by spunbonding.

12. The disposable garment of claim 1, wherein the first layer and the second layer are joined as two single layers.

13. The disposable garment of claim 1, wherein the first layer and the second layer form a single layer nonwoven web.

* * * * *